US009624259B2

(12) United States Patent
Seliktar et al.

(10) Patent No.: US 9,624,259 B2
(45) Date of Patent: Apr. 18, 2017

(54) COMPOSITIONS AND METHODS FOR SCAFFOLD FORMATION

(75) Inventors: Dror Seliktar, Haifa (IL); Maya Gonen-Wadmany, Haifa (IL)

(73) Assignee: Regentis Biomaterials Ltd., Or-Akiva (IL)

( * ) Notice: Subject to any disclaimer, the term of this patent is extended or adjusted under 35 U.S.C. 154(b) by 482 days.

(21) Appl. No.: 12/595,970

(22) PCT Filed: Apr. 16, 2008

(86) PCT No.: PCT/IL2008/000521
§ 371 (c)(1),
(2), (4) Date: Oct. 15, 2009

(87) PCT Pub. No.: WO2008/126092
PCT Pub. Date: Oct. 23, 2008

(65) Prior Publication Data
US 2010/0137510 A1 Jun. 3, 2010

Related U.S. Application Data

(60) Provisional application No. 60/907,765, filed on Apr. 16, 2007.

(51) Int. Cl.
*C07K 1/107* (2006.01)
*A61K 47/48* (2006.01)
*A61L 27/22* (2006.01)
*A61L 27/38* (2006.01)
*A61L 27/52* (2006.01)
*C07K 14/765* (2006.01)

(52) U.S. Cl.
CPC ...... *C07K 1/1077* (2013.01); *A61K 47/48215* (2013.01); *A61L 27/227* (2013.01); *A61L 27/38* (2013.01); *A61L 27/52* (2013.01); *C07K 14/765* (2013.01)

(58) Field of Classification Search
CPC ............... C07K 1/1077; C07K 14/765; A61K 47/48215; A61L 27/227; A61L 27/52; A61L 27/38
USPC .... 424/448, 449, 423, 422, 94.3, 78.1, 89.6, 424/499, 488; 525/54.1, 474, 477; 427/140; 524/405, 497, 588; 514/7.6, 514/13.7, 5.5, 2.3, 12, 56, 777, 54
See application file for complete search history.

(56) References Cited

U.S. PATENT DOCUMENTS

| 6,656,496 | B1 * | 12/2003 | Kilpadi | A61L 27/18 424/422 |
| 6,680,063 | B1 * | 1/2004 | Wadia et al. | 424/402 |
| 7,345,150 | B2 * | 3/2008 | Assaly et al. | 530/362 |
| 7,981,871 | B2 * | 7/2011 | Prestwich | A61L 27/20 424/488 |

| 2002/0019037 | A1 | 2/2002 | Caldwell et al. |
| 2005/0222083 | A1 | 10/2005 | Bulpitt et al. |
| 2006/0057070 | A1 | 3/2006 | Assaly et al. |
| 2006/0233854 | A1 | 10/2006 | Seliktar et al. |

FOREIGN PATENT DOCUMENTS

| GB | 1597757 | 9/1981 |
| WO | WO 95/15352 | 6/1995 |
| WO | WO 2005/056608 | 6/2005 |
| WO | WO 2005/061018 | 7/2005 |
| WO | WO 2007/050581 | 5/2007 |
| WO | WO 2008/126092 | 10/2008 |

OTHER PUBLICATIONS

F. Kratz et al., J. Med. Chem. 2000, 43, pp. 1253-1256.*
Dikovsky et al., Biomaterials 27 (2006) 1496-1506.*
International Preliminary Report on Patentability Dated Oct. 29, 2009 From the International Bureau of WIPO Re.: Application No. PCT/IL2008/000521.
International Search Report Dated Sep. 7, 2009 From the International Searching Authority Re.: Application No. PCT/IL2008/000521.
Written Opinion Dated Sep. 7, 2009 From the International Searching Authority Re.: Application No. PCT/IL2008/000521.
Communication Pursuant to Article 94(3) EPC Dated May 10, 2010 From the European Patent Office Re.: Application No. 08738223.0.
Response Dated Nov. 10, 2010 to Communication Pursuant to Article 94(3) EPC of May 10, 2010 From the European Patent Office Re.: Application No. 08738223.0.
Communication Pursuant to Rules 70(2) and 70a(2) EPC and Reference to Rule 39(1) EPC Dated Sep. 17, 2012 From the European Patent Office Re. Application No. 12167510.2.
European Search Report and the European Search Opinion Dated Aug. 16, 2012 From the European Patent Office Re. Application No. 12167510.2.
Carlsson et al. "Protein Thiolation and Reversible Protein-Protein Conjugation. N-Succinimidyl 3-(2-Pyridyldithio)Propionate, A New Heterobifunctional Reagent", Biochemical Journal, XP001146511, 173(3): 723-737, Jan. 1, 1978. Abstract, p. 726, 1-h Col., Para 2-P.734, 1-h Col., Para 1.
Mather et al. "Michael Addition Reactions in Macromolecular Design for Emerging Technologies", Progress in Polymer Science, XP027932369, 31(5): 487-531, May 1, 2006. Abstract, p. 523, Para 7—p. 525, Para 8.
Communication Pursuant to Article 94(3) EPC Dated Aug. 21, 2012 From the European Patent Office Re.: Application No. 08738223.0.
Carlsson et al. "Protein Thiolation and Reversible Protein-Protein Conjugation. N-Succinimidyl 3-(2-Pyridyldithio)Propionate, A New Heterobifunctional Reagent", Biochemical Journal, XP001146511, 173(3): 723-737, Jan. 1, 1978. Abstract, p. 726, 1-h Col., Para 2-p. 734, 1-h Col., Para 1.

(Continued)

*Primary Examiner* — Robert Jones, Jr.

(57) ABSTRACT

The present invention relates to scaffolds composed of a protein backbone cross-linked by a synthetic polymer. Specifically, the present invention provides PEGylated-thiolated collagen scaffolds and PEGylated albumin scaffolds and methods of generating and using same for treating disorders requiring tissue engineering.

8 Claims, 6 Drawing Sheets

(56) References Cited

OTHER PUBLICATIONS

Communication Pursuant to Article 94(3) EPC Dated Apr. 6, 2016 From the European Patent Office Re. Application No. 08738223.0.
Chen et al. "The Use of Bifunctional Polyethyleneglycol Derivatives for Coupling of Proteins to and Cross-Linking of Collagen Matrices", Journal of Materials Science: Materials in Medicine, XP008059254, 13(11): 1029-1035, Nov. 1, 2002.

* cited by examiner

COMPOSITIONS AND METHODS FOR SCAFFOLD FORMATION

RELATED APPLICATIONS

This Application is a National Phase of PCT Patent Application No. PCT/IL2008/000521 having International filing date of Apr. 16, 2008, which claims the benefit of U.S. Provisional Patent Application No. 60/907,765 filed on Apr. 16, 2007. The contents of the above Applications are all incorporated herein by reference.

FIELD AND BACKGROUND OF THE INVENTION

The present invention, in some embodiments thereof, relates to a scaffold comprising a protein cross-linked by a synthetic polymer, and more particularly, but not exclusively, to methods of generating and using same in tissue engineering.

Tissue engineering, i.e., the generation of new living tissues in vitro, is widely used to replace diseased, traumatized or other unhealthy tissues. The classic tissue engineering approach utilizes living cells and a basic scaffold for cell culture. Thus, the scaffold structure attempts to mimic the natural structure of the tissue it is replacing and to provide a temporary functional support for the cells.

Tissue engineering scaffolds are fabricated from either biological materials or synthetic materials, such as polymers. Synthetic materials such as polyethylene glycol (PEG), hydroxyapatite/polycaprolactone (HA/PLC), polyglycolic acid (PGA), poly-L-lactic acid (PLLA), polymethyl methacrylate (PMMA), polyhydroxyalkanoate (PHA), poly-4-hydroxybutyrate (P4HB), polypropylene fumarate (PPF), polyethylene glycol-dimethacrylate (PEG-DMA), beta-tricalcium phosphate (beta-TCP) and polytetrafluoroethylene (PTFE) provide precise control over the mechanical properties of the material [Drury and Mooney (2003)].

Common scaffold fabrication methods are based on foams of synthetic polymers. However, cell migration into the depth of synthetic scaffolds is limited by the lack of oxygen and nutrient supply. To overcome such limitations, new approaches utilizing solid freeform fabrications and internal vascular architecture have been developed [Sachlos and Czernuszka (2003)]. Likewise, freeze-drying methods are also employed to create unique three-dimensional architectures with distinct porosity and permeability.

Scaffolds made of PEG are highly biocompatible [Merrill and Salzman (1983)] and exhibit versatile physical characteristics based on their weight percent, molecular chain length, and cross-linking density [Temenoff et al. (2002)]. In addition, PEG hydrogels are capable of a controlled liquid-to-solid transition (gelation) in the presence of cell suspension [Elbert and Hubbell (2001)]. Moreover, the PEG gelation (i.e., PEGylation) reaction can be carried out under non-toxic conditions in the presence of a photoinitiator [Elisseeff et al. (2000); Nguyen and West (2002)] or by mixing a two-part reactive solution of functionalized PEG and cross-linking constituents [Lutolf and Hubbell (2003)].

A range of tissue engineering products based on collagen scaffolds are currently under development, some of which have reached the market. For example, collagen gels seeded with fibroblasts have been used as the "dermal" layer of the artificial skin sold under the tradename APLIGRAFT (Sandoz A G, Basel, Switzerland), and collagen sponges have been used as an osteoconductive carrier of bone morphogenic protein-2 (BMP-2) for spine fusion and the treatment of long bone fractures.

Collagen based biomaterials have been formed into fibers, film, sheets, sponges and dispersions of fibrils. Many of these forms could potentially be used as tissue engineering scaffolds in the repair or augmentation of body tissue.

Collagen gels are made from a network of fibrils that exhibit poor physical strength and super-physiological tissue porosity. The specific conformation of fibrils combined with the open pore structure of the interpenetrating network leaves the protein backbone easily accessible and susceptible to freely diffusing proteases from the surrounding host tissue or cell culture system. This often results in uncontrolled and premature deterioration of the scaffold in the presence of cell-secreted proteases [Hubbell (2003); Friess (1998); Nicolas and Gagnieu (1997)]. The discrepancies in structure and proteolytic susceptibility of reconstituted protein hydrogels compared to natural tissues still leaves much to be desired from the biologic scaffold systems in many practical tissue engineering applications.

Some techniques for improving the physical properties of collagen gels are based on covalent cross-links, using aldehydes, carbodiimides, and N-hydroxysuccinimides (NHS) [Park et al. (2002); Ma et al. (2004)], for example. Many of the cross-linking procedures offer some improvements over the physical stability and reduced enzymatic susceptibility of the scaffold, but do so by introducing a cytotoxic manufacturing step which requires extensive washes and increases the likelihood that residual toxins in the scaffold will affect cellular activity [Nimni et al. (1987); Friess (1998)].

Collagen and fibrin gels can also be processed by freeze-drying to increase the tensile strength and modulus of the protein network [Schoof et al. (2001); Buttafoco et al. (2006); Pieters et al. (2002)]. Fortier and coworkers have described a single-step process for generating a scaffold comprising albumin and polyethylene glycol, having an immobilized enzyme [Jean-Francois and Fortier (1996); Jean-Francois et al. (1997); Gayet and Fortier (1995); D'Urso et al. (1995)].

WO 1995/015352 describes a hydrogel comprising albumin and bifunctionalized polyethylene oxide.

WO 2005/061018 describes a scaffold comprising a naturally occurring protein such as fibrinogen cross-linked by PEG, by attaching modified PEG molecules to cysteine residues of the protein.

SUMMARY OF THE INVENTION

According to an aspect of some embodiments of the present invention there is provided a composition-of-matter comprising a polymer-protein precursor molecule which comprises a thiolated protein and at least two synthetic polymers covalently attached to thiol groups of the thiolated protein, each of the at least two synthetic polymers having a functional group, the functional group being selected capable of cross-linking with a functional group of at least one other synthetic polymer being covalently attached to at least one other polymer-protein precursor molecule so as to form a scaffold.

According to an aspect of some embodiments of the present invention there is provided a composition-of-matter comprising a polymer-protein precursor molecule which comprises albumin and at least two synthetic polymers covalently attached to the albumin, each of the at least two synthetic polymers having a functional group, the functional group being selected capable of cross-linking with a functional group of at least one other synthetic polymer being covalently attached to at least one other polymer-protein precursor molecule so as to form a scaffold.

According to an aspect of some embodiments of the present invention there is provided a scaffold formed by cross-linking a composition-of-matter described hereinabove.

According to an aspect of some embodiments of the present invention there is provided a scaffold comprising a plurality of thiolated proteins and a plurality of synthetic polymers covalently attached to thiol groups of the thiolated protein, each of the thiolated proteins being covalently attached to at least two of the synthetic polymers, wherein the synthetic polymers are cross-linked.

According to an aspect of some embodiments of the present invention there is provided a scaffold comprising a plurality of albumin molecules and a plurality of synthetic polymers covalently attached to the albumin molecules, each of the albumin molecules being covalently attached to at least two of the synthetic polymers, wherein the synthetic polymers are cross-linked.

According to an aspect of some embodiments of the present invention there is provided a hydrogel formed from a scaffold described hereinabove.

According to an aspect of some embodiments of the present invention there is provided a cosmetic composition comprising the hydrogel described hereinabove.

According to an aspect of some embodiments of the present invention there is provided a use of a composition-of-matter, scaffold or hydrogel described hereinabove for the manufacture of a medicament identified for repairing tissue damage.

According to some embodiments of the invention, the tissue damage is associated with a disorder selected from the group consisting of liver cirrhosis, Type-1 diabetes, cystic fibrosis, bone cancer, burn and wound repair, age related macular degeneration, scarring, myocardial infarction, myocardial repair, CNS lesions, articular cartilage defect, bladder degeneration and intestinal degeneration.

According to some embodiments of the invention, the medicament identified for repairing tissue damage is an adhesive.

According to some embodiments of the invention, the tissue damage is cosmetic.

According to some embodiments of the invention, the functional group is selected from the group consisting of acrylate and vinyl sulfone.

According to some embodiments of the invention, each of the synthetic polymers comprises from 1 to 7 acrylate groups.

According to an aspect of some embodiments of the present invention there is provided a method of generating a scaffold, the method comprising:

(a) thiolating a protein with a thiolating reagent, to thereby obtain a thiolated protein;

(b) covalently attaching a thiolated protein to at least two synthetic polymers through a first functional group of the at least two synthetic polymers, wherein the first functional group attaches to a thiol group of the thiolated protein, each of the at least two synthetic polymers having a second functional group, to thereby obtain a polymer-protein precursor molecule; and subsequently (c) cross-linking a plurality of the precursor molecules to thereby generate the scaffold.

According to some embodiments of the invention, the method described hereinabove further comprises combining live cells with the polymer-protein precursor molecules prior to step (c), to thereby obtain a scaffold comprising live cells embedded therein.

According to some embodiments of the invention, the method described hereinabove further comprises removing unconjugated form of the synthetic polymer prior to step (c).

According to an aspect of some embodiments of the present invention there is provided a method of generating a scaffold, the method comprising:

(a) covalently attaching albumin to at least two synthetic polymers through a first functional group of the at least two synthetic polymers, each of the at least two synthetic polymers having a second functional group, to thereby obtain a polymer-protein precursor molecule; and subsequently (b) cross-linking a plurality of the precursor molecules to thereby generate the scaffold.

According to some embodiments of the invention, the method described hereinabove further comprises removing the unconjugated form of the synthetic polymer prior to step (b).

According to some embodiments of the invention, the first functional group of the synthetic polymers is covalently attached to a cysteine residue of the albumin.

According to some embodiments of the invention, the first and second functional groups are identical.

According to some embodiments of the invention, the first and second functional groups are selected from the group consisting of acrylate and vinyl sulfone.

According to some embodiments of the invention, the synthetic polymers comprise PEG having from 2 to 8 acrylate groups.

According to some embodiments of the invention, the thiolated protein comprises thiolated lysine residues.

According to some embodiments of the invention, the protein is selected from the group consisting of a cell signaling protein, an extracellular matrix protein, a cell adhesion protein, a growth factor and a protease.

According to some embodiments of the invention, the protein comprises less than 5 cysteine residues per 100 amino acid residues.

According to some embodiments of the invention, the protein is collagen.

According to some embodiments of the invention, the protein is denatured.

According to some embodiments of the invention, the albumin is denatured.

According to some embodiments of the invention, the scaffold comprises at least 0.4% protein by dry weight.

According to some embodiments of the invention, the scaffold comprises at least 0.5% albumin by dry weight.

According to some embodiments of the invention, the scaffold or hydrogel described hereinabove further comprises live cells embedded therein.

According to some embodiments of the invention, the synthetic polymer is selected from the group consisting of polyethylene glycol (PEG), polycaprolactone (PLC), polyglycolic acid (PGA), poly-L-lactic acid (PLLA), polymethyl methacrylate (PMMA), polyhydroxyalkanoate (PHA), poly-4-hydroxybutyrate (P4HB), polypropylene fumarate (PPF) and polytetrafluoroethylene (PTFE), and copolymers thereof.

According to some embodiments of the invention, the synthetic polymer is PEG.

According to some embodiments of the invention, the PEG has a molecular weight in the range of 4 kDa to 20 kDa.

According to some embodiments of the invention, the functional group is selected capable of cross-linking with a functional group of at least one other synthetic polymer by chain polymerization.

According to some embodiments of the invention, the scaffold is biodegradable.

According to some embodiments of the invention, a concentration of the composition-of-matter is in a range of 1 mg/ml to 200 mg/ml.

According to some embodiments of the invention, the cross-linking is by ultraviolet illumination.

According to some embodiments of the invention, the cross-linking further comprises adding a photoinitiator.

According to some embodiments of the invention, the cross-linking further comprises cross-linking a plurality of the precursor molecules with a plurality of synthetic polymers, each of the synthetic polymers having at least two functional groups, the functional groups being selected capable of cross-linking with a functional group of the precursor molecules.

According to some embodiments of the invention, a concentration of the plurality of synthetic polymers is in a range of 1 mg/ml to 150 mg/ml.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying images. With specific reference now to the images in detail, it is stressed that the particulars shown are by way of example and for purposes of illustrative discussion of embodiments of the invention. In this regard, the description taken with the images makes apparent to those skilled in the art how embodiments of the invention may be practiced.

In the images:

FIG. 6A shows gradual increase in the distance covered by invading smooth muscle cells over the course of 5 days (scale bars equal 500 µm); FIG. 6B shows high magnification images of invaded areas in thiolated collagen and fibrinogen hydrogels (scale bars equal 100 µm); FIG. 6C presents a graph of the distances covered by invading smooth muscle cells in thiolated collagen and fibrinogen hydrogels as a function of time.

DESCRIPTION OF SPECIFIC EMBODIMENTS OF THE INVENTION

Figure 1:
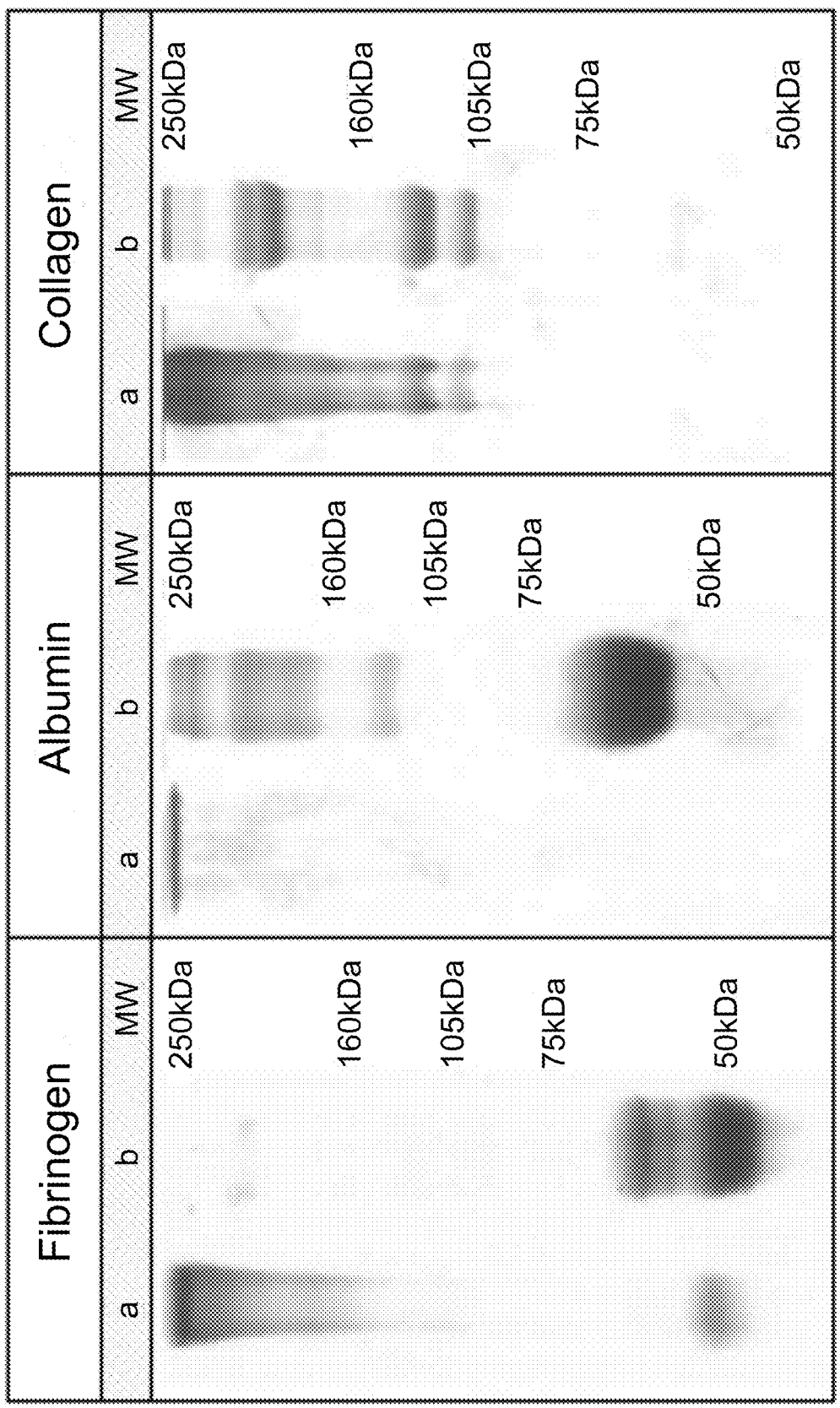
FIG. 1 present images presenting the results of SDS-polyacrylamide gel electrophoresis of PEGylated and non-PEGylated thiolated collagen, albumin and fibrinogen; lane "a" shows PEGylated protein and lane "b" shows non-PEGylated protein.

The present invention is of a scaffold comprising a protein cross-linked by a synthetic polymer, and more particularly, but not exclusively, to methods of generating and using same such as in tissue engineering.

The principles and operation of the method of generating a scaffold according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

While reducing the present invention to practice, the present inventors were able through laborious experimentation to synthesize biosynthetic hybrid scaffolds composed of a thiolated collagen or albumin backbone with functional polyethylene glycol (PEG) side chains. These scaffolds are excellent, biodegradable scaffolds and can be used in various clinical and research applications.

As is shown in the Examples section which follows, the present inventors generated PEG-collagen and PEG-albumin precursor molecules which were further used to form hydrogel scaffolds. The precursor molecules can be rapidly converted to a hydrogel (FIG. 2), and are biodegradable (FIG. 3). The PEG-collagen scaffolds exhibit strong support for cell spreading and extension (FIGS. 4C-D, 5D-F and 6A-C), whereas the PEG-albumin scaffolds exhibit resistance to cell spreading and extension (FIGS. 4A-B, 5A-C and 6A). The variety of properties exhibited allows one to select appropriate hydrogels for particular purposes, as well as to combine different types of precursor molecules in order to obtain hydrogels having intermediate properties.

Hence, according to one aspect of embodiments of the present invention there is provided a polymer-protein precursor molecule capable of cross-linking with at least one other polymer-protein precursor molecule so as to form a scaffold.

According to an optional embodiment of the present invention, the polymer-protein precursor molecule comprises a thiolated protein and at least two synthetic polymers covalently attached to thiol groups of the thiolated protein, each of the at least two synthetic polymers having a functional group, the functional group being selected capable of cross-linking with a functional group of at least one other synthetic polymer covalently attached to a thiolated protein of at least one other polymer-protein precursor molecule so as to form a scaffold.

As used herein, the term "thiolate" refers to the modification of a molecule (e.g., a protein) such that the modified molecule comprises more thiol groups than the non-modified molecule.

Various methods of thiolating a protein will be known to one skilled in the art. In an exemplary embodiment, lysine residues of the protein are thiolated by being covalently attached to a moiety (e.g., HS—CH$_2$—C(=O)—) comprising a thiol group. The amine groups of lysine residues are particularly suitable for reacting with a moiety comprising a thiol group, for example, by nucleophilic reaction with a thiolating reagent. As an example, the thiolation of collagen with succinimidyl acetylthioacetate (SATA) is demonstrated in the Examples hereinbelow (in the section titled "Collagen thiolation and PEGylation").

As used herein, the term "thiol" refers to a —SH group.

As used herein, a moiety said to be attached to a thiol group describes a S-M, wherein M is the moiety attached to a thiol group.

As used herein, the term "protein" encompasses any naturally occurring polypeptide comprising at least 10 peptide residues, as well as biologically active fragments thereof (e.g., fragments inducing cell adhesion and/or cell signaling). Biologically active fragments may be generated by any method known in the art (e.g., cleavage by an enzyme and/or a chemical reagent).

The thiolation of a protein is particularly suitable for producing the abovementioned composition-of-matter when the protein has a low cysteine content, as a non-protein with a low cysteine content typically has few thiol groups. Introduction of additional thiol groups by thiolating the protein creates additional sites available for linking synthetic polymers. Proteins having little or no cysteine (e.g., collagen) have heretofore not been suitable for inclusion in polymer-protein precursor molecules comprising synthetic polymers attached to cysteine residues of the protein. As many proteins have a low cysteine content, thiolation of a protein overcomes a serious drawback for polymer-protein precursor molecules.

Optionally, the protein to be thiolated comprises less than 5 cysteine residues per 100 amino acid residues. Optionally, the protein comprises less than 3 cysteine residues per 100 amino acid residues, optionally less than 2 cysteine residues per 100 amino acid residues, and optionally less than 1 cysteine residue per 100 amino acid residues.

According to an optional embodiment of the present invention, the protein to be thiolated is selected from the group consisting of a cell signaling protein, an extracellular matrix protein, a cell adhesion protein, a growth factor and a protease.

According to another optional embodiment of the present invention, the polymer-protein precursor molecule comprises an albumin molecule and at least two synthetic polymers covalently attached the albumin molecule, each of the at least two synthetic polymers having a functional group, the functional group being selected capable of cross-linking with a functional group of at least one other synthetic polymer covalently attached to an albumin molecule of at least one other polymer-protein precursor molecule so as to form a scaffold.

Optionally, the albumin is non-thiolated albumin.

According to an optional embodiment of the present invention, the thiolated protein is thiolated collagen.

According to an optional embodiment of the present invention, the albumin and/or thiolated protein are denatured.

Without being bound by any particular theory, it is believed that denatured proteins typically have more sites available for attaching to synthetic polymers.

Proteins may be denatured by various methods well known in the art. For example, proteins can be denatured by heating or exposure to denaturing agents such as urea or guanidinium chloride. As exemplified hereinbelow, the protein may be denatured in a solution comprising 8 M urea.

The term "polymer" refers to a molecule composed primarily of a plurality of repeating units. The phrase "synthetic polymer" refers to any polymer which is made of a synthetic material, i.e., a non-natural, non-cellular material.

The synthetic polymers of this aspect of the present invention may be identical or different. Each of the synthetic polymers in the composition-of-matter may optionally comprise a functional group which attaches the synthetic polymer to the albumin and/or thiolated protein.

Optionally, the synthetic polymer is suitable for tissue engineering, for example, a polymer that is relatively non-harmful when implanted in a subject. Suitable synthetic polymers include, without limitation, polyethylene glycol (PEG), polycaprolactone (PLC), polyglycolic acid (PGA), poly-L-lactic acid (PLLA), polymethyl methacrylate (PMMA), polyhydroxyalkanoate (PHA), poly-4-hydroxybutyrate (P4HB), polypropylene fumarate (PPF) and polytetrafluoroethylene (PTFE), and copolymers thereof. In exemplary embodiments, the synthetic polymer is PEG. The PEG may be linear or branched. Optionally, the PEG has a molecular weight in the range of 4 kDa to 20 kDa.

It is to be understood that the names of the abovementioned polymers refer to the repeating units which make up the majority of the structure of the synthetic polymers, and are not meant to exclude the presence of additional functional groups in the synthetic polymer. Thus for example, a synthetic polymer consisting of polyethylene glycol with two acrylate groups (i.e., PEG-diacrylate) is encompassed herein by the terms "polyethylene glycol" and "PEG".

Exemplary functional groups capable of cross-linking include, without limitation, acrylate and vinyl sulfone.

Methods of preparing functionalized PEG molecules are known in the arts. For example, PEG-vinyl sulfone can optionally be prepared under argon by reacting a dichloromethane (DCM) solution of the PEG-OH with NaH and then with divinylsulfone (optionally at molar ratios: OH 1:NaH 5:divinyl sulfone 50, and with 0.2 gram PEG per ml of DCM). PEG-Ac may optionally be made under argon by reacting a DCM solution of the PEG-OH with acryloyl chloride and triethylamine (optionally at molar ratios: OH 1:acryloyl chloride 1.5:triethylamine 2, and with 0.2 gram PEG per ml of DCM).

According to an optional embodiment of the present invention, the functional group of the synthetic polymer is capable of cross-linking with a functional group of at least one other synthetic polymer by chain polymerization.

As used herein, the phrase "chain polymerization" describes the linking together of a plurality (optionally at least 10) of unsaturated and/or cyclic monomers. Chain polymerization of unsaturated monomers results in replacement of unsaturated bonds with bonds linking the monomers. Chain polymerization of saturated cyclic monomers results in ring-opening of the cyclic monomers.

In the context of embodiments of the present invention, the monomers capable of undergoing chain polymerization are functional groups of the synthetic polymer described hereinabove, whereby polymerization of functional groups cross-links the synthetic polymers comprising the functional groups, and consequently, the polymer-protein precursor molecules comprising the synthetic polymers.

The synthetic polymers may have one or more functional groups. Optionally, the synthetic polymers comprise from 1 to 7 functional groups. According to exemplary embodiments, the functional groups are acrylate groups.

Thus for example, linear PEG may be attached to a thiolated protein at one end, and be attached at the other end to an acrylate group (e.g., $-OC(=O)-CH=CH_2$). 4-armed branched PEG may be attached at one end to a thiolated protein, and be attached at the other 3 ends to acrylate groups. 8-armed branched PEG may be attached at one end to a thiolated protein, and be attached at the other 7 ends to acrylate groups. Hence, PEG molecules having from 2 to 8 ends are particularly suitable for comprising from 1 to 7 functional groups.

As described hereinabove, the compositions-of-matter of embodiments of the present invention are capable of cross-linking so as to form a scaffold.

Hence, according to another aspect of embodiments of the present invention, there is provided a scaffold comprising protein covalently attached to cross-linked synthetic polymers. Optionally, the scaffold comprises more than one type of protein and/or more than one type of synthetic polymer.

According to an optional embodiment of the present invention, the scaffold comprises a plurality of thiolated proteins and a plurality of synthetic polymers covalently attached to thiol groups of the thiolated protein, each of the thiolated proteins being covalently attached to at least two of the synthetic polymers, wherein the synthetic polymers are cross-linked.

According to another optional embodiment of the present invention, the scaffold comprises a plurality of albumin molecules and a plurality of synthetic polymers covalently attached to the albumin molecules, each of the albumin molecules being covalently attached to at least two of the synthetic polymers, wherein the synthetic polymers are cross-linked with each other.

According to some embodiments of the present invention, there is provided a scaffold formed by cross-linking a composition-of-matter described hereinabove.

As used herein the phrase "scaffold" refers to a two-dimensional or a three-dimensional supporting framework. By controlling cross-linking, the scaffold of the present invention can form two- or three-dimensional structure at any size, structure or porosity. The scaffold of the present invention can be embedded within, or formed around, another scaffold or gel or it can be linked to additional materials to form a hybrid or coated scaffold.

In some embodiments of the present invention, the scaffold of the present invention can be used to support cell growth, attachment, spreading, and thus facilitate cell growth, tissue regeneration and/or tissue repair.

In alternative embodiments of the present invention, the scaffold can be used as an adhesive, and thus facilitate tissue repair. Optionally, the adhesive does not support cell growth.

According to an optional embodiment of the present invention, the scaffold is biodegradable.

As used herein, the terms "biodegradable" and "biodegradability" refer to being capable of being degraded (i.e., broken down) by biological proteases or other biomolecules. Biodegradability depends on the availability of degradation substrates (i.e., biological materials or portion thereof), the presence of biodegrading materials (e.g., microorganisms, enzymes, proteins) and the availability of oxygen (for aerobic organisms, microorganisms or portions thereof), carbon dioxide (for anaerobic organisms, microorganisms or portions thereof) and/or other nutrients. In addition, biodegradability of a material, such as the scaffold of the present invention, also depends on the material structure and/or mechanical properties, i.e., the porosity, flexibility, viscosity, cross-link density, hydrophobicity/hydrophilicity, and elasticity which may affect passage and availability of gasses and nutrients, as well as cell attachment and spreading.

The biodegradability of the scaffold derives at least in part from the biodegradability of the protein in the scaffold, which forms the backbone of the scaffold. As exemplified in the Examples section hereinbelow, the biodegradability of the scaffold can be determined by selecting a protein which provides a particular level of biodegradability. Furthermore, the biodegradability can be determined by selecting a biodegradable or non-biodegradable synthetic polymer. Biodegradability is also affected by the number of synthetic molecules attached to each protein, as large numbers of attached synthetic molecules may reduce biodegradability by masking cleavage sites.

The biodegradability of a hydrogel scaffold of embodiments of the present invention can be determined by subjecting such hydrogels to enzymatic degradation using proteases such as plasmin, trypsin, collagenase, chemotrypsin and the like, as exemplified hereinbelow in the Examples section.

In general, the biological and mechanical properties of the scaffold will be determined in part by the ratio of protein to synthetic polymer in the scaffold. For example, scaffolds with a high protein content will exhibit the biological properties, such as cell signaling, of the proteins contained therein, while retaining the advantageous mechanical properties characteristic of the synthetic polymer contained therein. Optionally, the scaffold comprises at least 0.4% thiolated protein by dry weight, optionally at least 1.5%, optionally at least 4%, optionally at least 10%, and optionally at least 20%. Optionally, the scaffold comprises at least 0.5% albumin by dry weight, optionally at least 1.5%, optionally at least 4%, optionally at least 10%, and optionally at least 20%. Exemplary scaffolds comprise PEG and protein (e.g., thiolated collagen or albumin) at a molar ratio ranging from 25:1 PEG per protein to 300:1 PEG per protein.

In many cases, it is desirable to have live cells grow in the space filled by a scaffold used in tissue engineering. This is facilitated by having live cells seeded in the scaffold. One advantage of embodiments of the present invention is that the scaffold may be formed from a liquid phase (e.g., a solution of a polymer-protein precursor molecule), using mild conditions to initiate cross-linking. Consequently, live cells may be dispersed among the precursor molecules, resulting in a scaffold having live cells embedded therein, as cross-linking can be performed with mild conditions that do not harm the cells.

Hence, according to an optional embodiment of the present invention, the scaffold comprises live cells embedded therein. Optionally, the scaffold with live cells embedded therein comprises thiolated protein.

Exemplary cells suitable for inclusion in embodiments of the present invention are capable of forming a tissue, including, without limitation, stem cells such as embryonic stem cells, bone marrow stem cells, cord blood cells, mesenchymal stem cells, adult tissue stem cells; or differentiated cells such as neural cells, retinal cells, epidermal cells, hepatocytes, pancreatic (islet) cells, osseous cells, cartilaginous cells, elastic cells, fibrous cells, myocytes, myocardial cells, endothelial cells, smooth muscle cells, and hematopoietic cells.

As used herein, the term "seeding" refers to encapsulating, entrapping, plating, placing and/or dropping cells into the scaffold of the present invention. It will be appreciated that the concentration of cells which are seeded on or within the scaffold of the present invention depends on the type of cells used and the composition of scaffold used (i.e., molar ratio between the synthetic polymer and protein within the precursor molecules and the percent of cross-linking molecule used).

It will be appreciated that seeding of the cells can be performed following the formation of the scaffold or hydrogel formed from the scaffold (as described hereinbelow), or by mixing the cells with the precursor molecules prior to the cross-linking which generates the scaffold. The concentration of cells to be seeded on the scaffold and/or hydrogel depends on the cell type and the properties of the scaffold and/or hydrogel, and those of skills in the art are capable of determining a suitable concentration of cells in each case.

It will be appreciated that following seeding the cells on the scaffold and/or hydrogel, the cells are optionally cultured in the presence of tissue culture medium and growth factors, in order to maintain their viability.

The scaffold and/or hydrogel may be examined (e.g., using an inverted microscope) following seeding, in order to evaluate cell growth, spreading and tissue formation, as exemplified in the Examples section.

As exemplified in the Examples section hereinbelow, scaffolds of embodiments of the present invention can form hydrogels, for example by combining the scaffold with an aqueous liquid.

Hence, according to another aspect of embodiments of the present invention, there is provided a hydrogel formed from a scaffold described hereinabove.

According to another aspect of embodiments of the present invention, there is provided a cosmetic composition comprising a hydrogel described hereinabove.

The properties of a hydrogel will be determined in part by the concentration of a composition-of-matter in the hydrogel. Briefly, higher concentrations of composition-of-matter result in hydrogels with a higher degree of cross-linking, higher mechanical strength and lower porosity, whereas lower concentrations of composition-of-matter result in hydrogels with less cross-linking, lower mechanical strength and high porosity.

According to an optional embodiment of the present invention, the hydrogel comprises the composition-of-matter at a concentration in a range of 1 mg/ml to 200 mg/ml. Optionally, the concentration is in a range of 3 mg/ml to 50 mg/ml, and optionally from 3 mg/ml to 30 mg/ml.

As described herein, and exemplified in the Examples section below, the polymer-protein precursor molecules described hereinabove allow one to generate a scaffold in a simple and convenient manner. Furthermore, it is conveniently possible to adjust the biological and mechanical properties of the scaffold by modifying the protein to polymer ratio, the concentration of precursor molecules and so forth, as described herein.

Hence, according to another aspect of the present invention, there is provided a method of generating a scaffold.

According to an optional embodiment of the present invention, the method is of generating a scaffold comprising a thiolated protein, the method comprising thiolating a protein with a thiolating reagent, to thereby obtain a thiolated protein; covalently attaching a thiolated protein to at least two synthetic polymers through a first functional group of the at least two synthetic polymers, wherein the first functional group attaches to a thiol group of the thiolated protein, each of the at least two synthetic polymers having a second functional group, to thereby obtain a polymer-protein precursor molecule; and subsequently cross-linking a plurality of the precursor molecules to thereby generate the scaffold.

According to another optional embodiment of the present invention, the method is of generating a scaffold comprising albumin, the method comprising covalently attaching albumin to at least two synthetic polymers through a first functional group of the at least two synthetic polymers, each of the at least two synthetic polymers having a second functional group, to thereby obtain a polymer-protein precursor molecule; and subsequently cross-linking a plurality of the precursor molecules to thereby generate said scaffold. Optionally, the first functional group of the synthetic polymers is covalently attached to a cysteine residue (e.g., to the thiol group of cysteine) of the albumin. Cysteine residues may be reduced, so that the cysteine residues will be in the thiol form, and not in a disulfide form. Optionally, a non-titered solution of albumin is used for attaching to the synthetic polymer.

Exemplary first functional groups (i.e., groups capable of attaching to the albumin and/or thiolated protein) include without limitation, acrylate, aldehye, tosyl, tresyl, dichlorotriazine, epoxide, succinimidyl succinate, succinimidyl ester, p-nitrophenyl carbonate, benzotriazolyl carbonate, 2,3,5-trichlorophenyl carbonate, succinimidyl carbonate, pyridyldisulfide, maleimide, vinylsulfone, and iodoacetamide.

According to optional embodiments of the present invention, the abovementioned first functional group and second functional group are identical to each other.

The first functional group must be capable of attaching to the protein, whereas the second functional group must be capable of cross-linking with other second functional groups. Thus, any functional group capable of both attaching to albumin and/or a thiolated protein, and cross-linking with like groups, may be used as both the first functional group and the second functional group. Exemplary groups include, without limitation, acrylate and vinyl sulfone. Thus, for example, the double bond of acrylate and vinyl sulfone may be attached to albumin and/or thiolated protein (e.g., to a thiol group of the protein) by a Michael-like addition reaction, and may be cross-linked with the double bond of other functional groups by chain polymerization.

According to an optional embodiment of the present invention, the synthetic polymer comprises PEG. Optionally, the PEG has from 2 to 8 acrylate groups. Optionally, the 2 to 8 acrylate groups include the first and second functional groups described hereinabove.

The methods described hereinabove may optionally be carried out such that the percentage of synthetic polymers attached to the protein (i.e., albumin and/or thiolated protein) at a single site is maximized, and the percentage of synthetic polymers attached to the protein at more than one site is minimized. This may be achieved, for example, by reacting the protein with an excess of synthetic polymer, as exemplified hereinbelow. Thus, for example, a PEG molecule having 2 to 8 acrylate groups would attach to the protein via a single acrylate, leaving 1 to 7 acrylate groups available for cross-linking.

Due to the ease of cross-linking of the precursor molecules of embodiments of the present invention so as to form a scaffold, cross-linking of the precursor molecules may be performed either inside (i.e., in vivo) or outside of a body. Cross-linking in vivo, for example, may be used to generate a scaffold having the exact shape of the cavity in the body that is to be filled with the scaffold.

Various methods of cross-linking are known in the art. For example, cross-linking may be effected by illumination (e.g., by ultraviolet light), by chemical reagents (e.g., free radical donors) and/or heat.

According to an optional embodiment of the present invention, the cross-linking is by illumination with ultraviolet light (e.g., at a wavelength of about 365 nm).

As used herein the term "about" refers to ±10%.

When cross-linking in vivo, it is preferable to avoid doses of ultraviolet light that are harmful. The maximal dose which is non-harmful will depend, for example, on the wavelength of ultraviolet light used, and on the part of the body exposed to ultraviolet light. One skilled in the art will readily be capable of determining whether a dose is harmful or non-harmful.

Optionally, a photoinitiator is added to facilitate cross-linking. Addition of a photoinitiator will typically enable one to use lower doses of ultraviolet light for cross-linking.

As used herein, the term "photoinitiator" describes a compound which initiates a chemical reaction (e.g., cross-linking reaction, chain polymerization) when exposed to ultraviolet illumination. Many suitable photoinitiators will be known to one skilled in the art. Exemplary photoinitiators include, without limitation, bis(2,4,6-trimethylbenzoyl) phenylphosphine oxide (BAPO), 2,2-dimethoxy-2-phenylacetophenone (DMPA), camphorquinone (CQ), 1-phenyl-1,2-propanedione (PPD), the organometallic complex Cp'Pt(CH(3))(3) (Cp'=eta(5)–C(5)H(4)CH(3)), 2-hydroxy-1-[4-(hydroxyethoxy)phenyl]-2-methyl-1-propanone (e.g., Irgacure™ 2959), dimethylaminoethyl methacrylate (DMAEMA), 2,2-dimethoxy-2-phenylacetophenone, benzophenone (BP), and flavins.

According to an optional embodiment of the present invention, unconjugated synthetic polymer molecules (i.e., synthetic polymer molecules which failed to attach to the protein) are removed from the precursor molecules prior to cross-linking of the precursor molecules.

According to an optional embodiment of the present invention, cross-linking of precursor molecules further comprises cross-linking of the precursor molecules with a plurality of synthetic polymers, each of the synthetic polymers having at least two functional groups, the functional groups being selected capable of cross-linking with a functional group of the precursor molecules. Optionally, the plurality of synthetic polymers is in a range of 1 mg/ml to 150 mg/ml, optionally in a range of 2 mg/ml to 50 mg/ml, and optionally in a range of 5 mg/ml to 15 mg/ml. Suitable synthetic polymers and functional groups for cross-linking are as described hereinabove.

Addition of synthetic polymer will increase the mechanical strength of the scaffold that is generated. If the synthetic polymer is non-biodegradable, the biodegradability of the scaffold will be reduced. Thus, the properties of the scaffold can be modified as desired by adding an appropriate amount of synthetic polymer to be cross-linked with the precursor molecules.

Optionally, the unconjugated synthetic polymer (i.e., synthetic polymer that is not a component of a precursor molecule) is less than 20%, optionally less than 15%, optionally less than 10%, and optionally less than 5%, of the total weight of all the material (e.g., precursor molecules and unconjugated synthetic polymer) being cross-linked to form a scaffold.

It is to be noted that one may remove unconjugated synthetic polymer prior to cross-linking of the precursor molecules, and then add the same unconjugated synthetic polymer to be cross-linked with the precursor molecules. For example, it may be desirable to remove unconjugated synthetic polymer of which the concentration is uncertain, and then add unconjugated synthetic polymer at a known concentration.

Embodiments of the present invention may optionally further include components which are nonreactive to the scaffold and/or hydrogel. Examples of such nonreactive components include, without limitation, drugs such as disinfectants, chemotherapeutics, antimicrobial agents, antiviral agents, hemostatics, antiphlogistics, anesthetics, analgesics, nutritional supplements, biopolymers such as peptides, plasma derivative proteins, enzymes or mixtures thereof.

Such components may be included in the hydrogel, for example, by dissolving or suspending the nonreactive components in the aqueous liquid comprised by the hydrogel. Methods of loading hydrogels with pharmaceuticals are well known in the art.

In addition, the biofunctionality of the scaffold and/or hydrogel described hereinabove can be further increased by attaching or impregnating a protein such as a cell signaling protein, or a growth factor (e.g. a nerve growth factor) to the hydrogel.

Attaching such proteins to the hydrogel scaffold of the present invention is optionally employed by cross-linking a precursor molecule comprising the desired protein with the other precursor molecules of the scaffold. Optionally, the additional precursor molecule is any precursor molecule described hereinabove. Alternatively, the precursor molecule is one described, for example, in WO 2005/061018.

Alternatively, the hydrogel may be impregnated with a desired protein by dehydrating the scaffold and then immersing the hydrogel in a solution containing the desired protein and gently shaking for a few hours until the desired protein penetrate the scaffold during the hydration process. Likewise, the hydrogel can be impregnated with a desired protein by incubation in a solution comprising the desired protein until the protein diffuses into the polymeric network of the scaffold by slow, passive diffusion. The latter is influenced by the degree of cross-linking, the porosity of the scaffold, and the structural properties described herein.

Apart from being inexpensive to produce, the scaffold of the present invention is highly reproducible, flexible (can be stressed or stretched easily), exhibits controllable structural properties, and is amenable to controllable biodegradation; characteristics which make it highly suitable for in vivo or ex vivo engineering of tissues such as bone, nerve, cartilage, heart muscle, skin tissue, blood vessels, and other tissues (soft and hard) in the body. For example, a scaffold and/or hydrogel according to embodiments of the present invention can be easily placed into gaps within a tissue or an organ, following which it can fill the void and initiate the process of regeneration as the scaffold degrades away.

Hence, according to another aspect of embodiments of the present invention, there is provided the use of a composition-of-matter and/or scaffold and/or hydrogel described hereinabove for the manufacture of a medicament identified for repairing tissue damage.

Examples for disorders or conditions in which repairing tissue damage is beneficial include, but are not limited to, liver cirrhosis such as in hepatitis C patients (liver), Type-1 diabetes (pancreas), cystic fibrosis (lung, liver, pancreas), bone cancer (bone), burn and wound repair (skin), age related macular degeneration (retina), myocardial infarction, myocardial repair, CNS lesions (myelin), articular cartilage defects (chondrocytes), bladder degeneration, intestinal degeneration, and the like. In addition, repairing tissue damage which is cosmetic is frequently beneficial.

As used herein, the term "cosmetic" refers to apparent (e.g., visible) tissue, including, but not limited to, skin tissue. Cosmetic tissue damage is typically detrimental aesthetically, and may be detrimental for additional reasons (e.g. psychological factors).

The phrase "in vivo" refers to within a living organism such as a plant or an animal, preferably in mammals, preferably, in human subjects.

As used herein, the term "subject" refers to a vertebrate, preferably a mammal, more preferably a human being (male or female) at any age.

The scaffold of the present invention can be implanted in the subject using a surgical tool such as a scalpel, spoon, spatula, or other surgical device.

It will be appreciated that in vivo formation of a tissue can be also achieved by administering the precursor molecules to the subject and further cross-linking the precursor molecules in vivo. Cross-linking can be performed as described hereinabove using non-toxic, non-hazardous agents and/or conditions.

The scaffold and/or hydrogel of the present invention can be also used for ex vivo formation of a tissue.

As used herein, the phrase "ex vivo" refers to living cells which are derived from an organism and are growing (or cultured) outside of the living organism, preferably, outside the body of a vertebrate, a mammal, or human being. For example, cells which are derived from a human being such as human muscle cells or human aortic endothelial cells and are cultured outside of the body are referred to as cells which are cultured ex vivo.

It will be appreciated that cells seeded on the scaffold for ex vivo formation of a tissue can be derived from the treated individual (autologous source) or from allogeneic sources such as embryonic stem cells which are not expected to induce an immunogenic reaction.

Following ex vivo tissue formation the seeded scaffold is implanted in the subject. Those of skills in the art are capable of determining when and how to implant the scaffold to thereby induce tissue regeneration and treat the disease.

For example, for articular cartilage the scaffold is optionally seeded with chondrocytes, and following 14-21 days in culture the scaffold may be implanted in the articular surface of the joint thereafter.

Alternatively, the scaffold can be injected as a precursor solution, with or without cells, and polymerized directly in the site of the cartilage damage. The polymerized hydrogel fills the gap of the defect and initiates the regeneration of new cartilage tissue.

As used herein, the phrase "tissue" refers to part of an organism consisting of an aggregate of cells having a similar structure and function. Examples include, but are not limited to, brain tissue, retina, skin tissue, hepatic tissue, pancreatic tissue, bone, nerve, cartilage, connective tissue, blood tissue, muscle tissue, cardiac tissue brain tissue, vascular tissue, renal tissue, pulmonary tissue, gonadal tissue, hematopoietic tissue and fat tissue. Preferably, the phrase "tissue" as used herein also encompasses the phrase "organ" which refers to a fully differentiated structural and functional unit in an animal that is specialized for some particular function. Non-limiting examples of organs include head, brain, eye, leg, hand, heart, liver kidney, lung, pancreas, ovary, testis, and stomach.

In certain embodiments of the present invention the tissue is an acellularized tissue, i.e., does not comprise cells.

As exemplified in the Examples section herein, precursor molecules comprising albumin as the protein result in hydrogels that are relatively resistant to cell invasion. Such hydrogels may be used for example, as an adhesive. In contrast, as further exemplified herein, precursor molecules comprising an extracellular matrix protein (e.g., thiolated collagen) result in a hydrogel which is readily degraded and invaded by cells. Such hydrogels may be used for example, when it is desirable that the hydrogel by replaced by natural tissue.

Medicaments according to embodiments of the present invention may optionally be presented in a pack or dispenser device, such as an FDA-approved kit, which may contain one or more unit dosage forms (e.g., 100 mg) such as for personalized use containing the active ingredient (e.g., precursor molecules which are not yet cross-linked) and optionally sterile disposable means for delivery (e.g., syringe) and for illumination (e.g., illuminator covers). The pack may, for example, comprise metal or plastic foil, such as a blister pack. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising a preparation of the invention formulated in a pharmaceutically acceptable carrier may also be prepared, placed in an appropriate container, and labeled for treatment of an indicated condition, as further detailed above.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

The terms "comprises", "comprising", "includes", "including", "having" and their conjugates mean "including but not limited to".

The term "consisting of" means "including and limited to".

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

Examples

Reference is now made to the following examples, which together with the above descriptions illustrate some embodiments of the invention in a non limiting fashion.

Peg-Diacrylate Synthesis:

PEG-diacrylate (PEG-DA) was prepared from linear 10 kDa PEG-OH (Fluka, Aldrich) as described elsewhere. Briefly, acrylation of PEG-OH was carried out under argon by reacting a dichloromethane solution of PEG-OH with acryloyl chloride (Merck) and triethylamine (Fluka) at a molar ratio of 1.5:1 acryloyl chloride to OH groups. The final product was precipitated in ice-cold diethyl ether and dried under vacuum for 48 hours. $^1$H-NMR spectroscopy was used to verify end-group conversion and purity of the final product.

Collagen Thiolation and PEGylation:

Collagen (type I) was isolated from rat tail tendon according to published protocols. Thiolation of collagen was accomplished using succinimidyl-acetyl-thioacetate (SATA) (Pierce) as described by Chen et al. (2002). Briefly, collagen was dissolved in 150 mM phosphate-buffered saline (PBS) with 8 M urea at a concentration of 5 mg/ml. SATA was reacted with the collagen for 2 hours at room temperature with agitation at a concentration of 0.075 mg per mg collagen. The resulting acetylated —SH groups attached to lysine residues were then deprotected by the reacting the collagen with 0.5 M hydroxylamine hydrochloride (Sigma-Aldrich) for 2 hours at a concentration of 0.125 ml per mg collagen. The product was dialyzed overnight against PBS with 8 M urea.

The thiolated collagen was PEGylated by reacting with TCEP-HCl (tris(2-carboxyethyl)phosphine hydrochloride) at a 2:1 molar ratio of TCEP to thiol groups of the thiolated collagen. The thiolated collagen was then reacted for 3 hours with 10 kDa PEG-DA at a molar ratio of 1.5:1 PEG-DA per thiol group at pH 8 and room temperature. The PEGylated thiolated collagen was precipitated in acetone and redissolved in PBS with 8 M urea and dialyzed in a Slide-A-Lyzer (10,000 MWCO, Pierce) at 37° C. for 2 days to a final concentration of 4 mg/ml collagen. The PEGylated product was characterized according to published protocols.

Albumin and Fibrinogen PEGylation:

Albumin was PEGylated without thiolation, in order to prepare hydrogels from PEGylated albumin. Fibrinogen was PEGylated and used to prepare hydrogels for the sake of comparison with albumin and thiolated collagen.

Bovine fibrinogen (Sigma-Aldrich) and bovine serum albumin (MP Biomedicals) were each dissolved in 150 mM PBS with 8 M urea to give 7 mg/ml solutions. TCEP-HCl was added to the protein solutions at a molar ratio of 1.5:1 TCEP to fibrinogen cysteines and at a 2:1 ratio to albumin cysteines. After dissolution, a solution of 280 mg/ml PEG-DA (linear PEG-diacrylate, 10 kDa) in 150 mM PBS with 8 M urea was added and reacted for 3 hours at room temperature. The molar ratio of PEG to fibrinogen cysteines was 4:1. The molar ratio of PEG to albumin cysteines was 2:1. After the incubation, the PEGylated proteins were diluted with an equal volume of 150 mM PBS containing 8 M urea and precipitated by adding 5 volumes of acetone. The precipitates were redissolved in PBS containing 8 M urea using a homogenizer, at ~2 mg/ml protein concentration for albumin, and at ~7 mg/ml for fibrinogen, and dialyzed against 150 mM PBS at 4° C. for 2 days with two changes of PBS. The PEGylated protein solutions were then lyophilized for at least 2 days and redissolved in 150 mM PBS to reach a protein concentration of ~8 mg/ml.

SDS-PAGE Analysis of Protein PEGylation:

The PEGylation reaction was confirmed by SDS-PAGE (sodium dodecyl sulfate-polyacrylamide gel electrophoresis). This is a straightforward method for qualitatively evaluating PEGylation of proteins, as the grafting of PEG onto a protein has a detectable effect on the mobility of the protein in polyacrylamide gel. PEGylated and non-PEGylated protein was loaded into 8% polyacrylamide gels. The gels were stained with Coomassie® blue and digitally imaged using a gel documentation workstation.

As shown in FIG. 1, PEGylation of albumin, thiolated collagen and non-thiolated fibrinogen caused a marked increase in the apparent MW. The PEGylated albumin, collagen and fibrinogen are visible as a continuous smear at the top-most portion of the gel. Some of the collagen and fibrinogen remained un-PEGylated as indicated by the collagen band at approximately 105 kDa and by the fibrinogen band around 50 kDa.

Hydrogel Formation:

PEGylated protein precursors were formed into hydrogels by photopolymerization using 0.1% (w/v) Irgacure™ 2959 (Ciba Specialty Chemicals) and exposure to ultraviolet light (365 nm, 4-5 mW/cm$^2$) for 5 minutes. All tissue culture experiments were performed with 4 mg/ml PEGylated protein precursor supplemented with 10 mg/ml of linear PEG-DA (10 kDa).

Hydrogel formation was confirmed by strain-rate controlled shear rheometry. Dynamic time sweep tests in plate-plate geometry were performed at 37° C., at a constant frequency of 1 radian/second and a sinusoidal strain of 5% using an Advanced Rheometric Expansion System (ARES, Rheometer Scientific). The storage (G') and loss (G") moduli were recorded as a function of time for up to 10 minutes by RSI Orchestrator 6.5.8 software. After 20 seconds, the solution was polymerized by photoinitiation using an ultraviolet light source (4-5 mW/cm$^2$). The reported shear modulus was taken as a real part of the complex shear modulus G*=G'+iG" at the conclusion of the time-sweep test.

Figure 2:
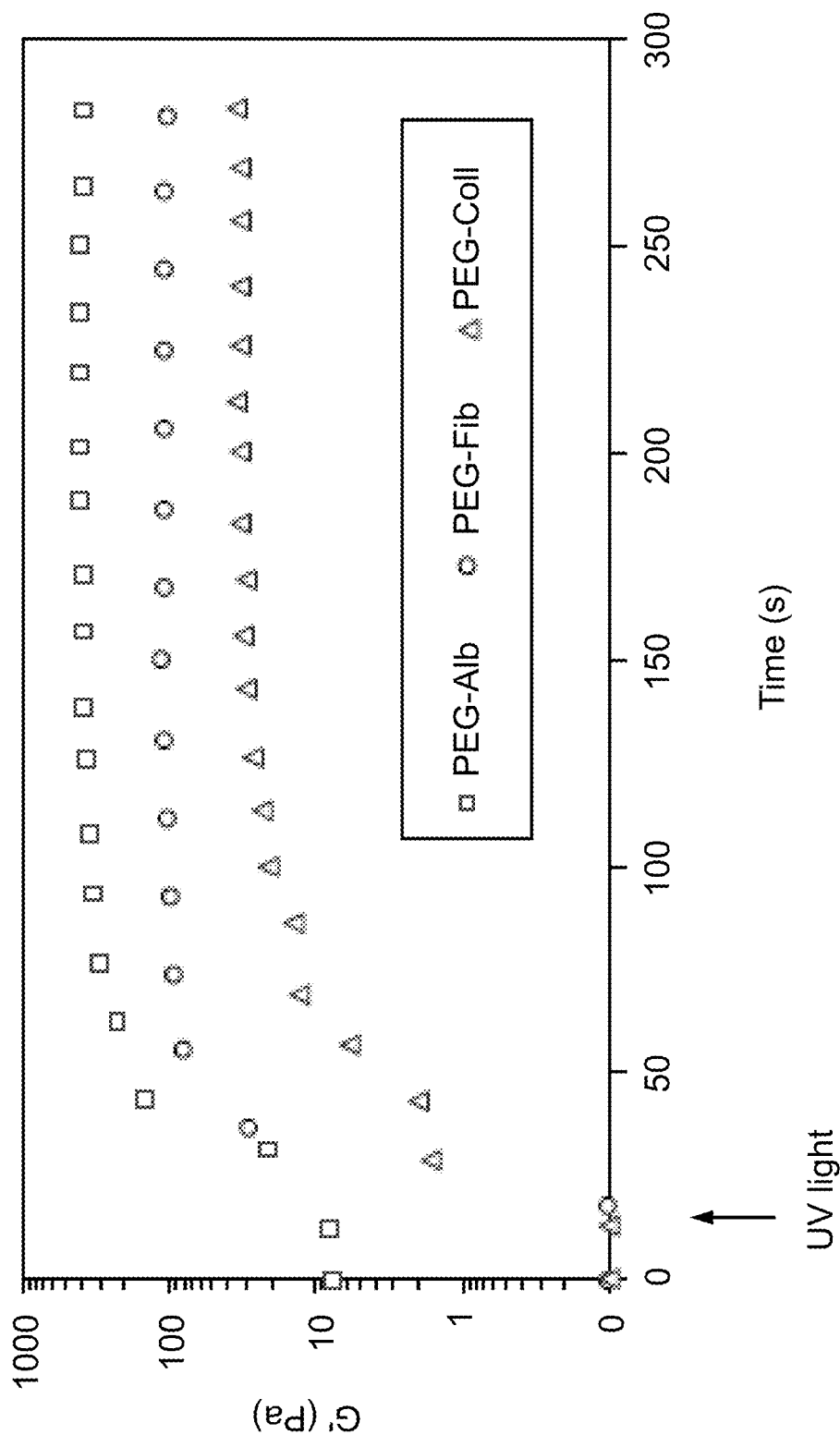
FIG. 2 presents a graph showing the storage modulus (G') of PEGylated albumin (PEG-Alb), PEGylated fibrinogen (PEG-Fib) and PEGylated thiolated collagen (PEG-Coll) as a function of time, before and during ultraviolet (UV) illumination.
Figure 3:
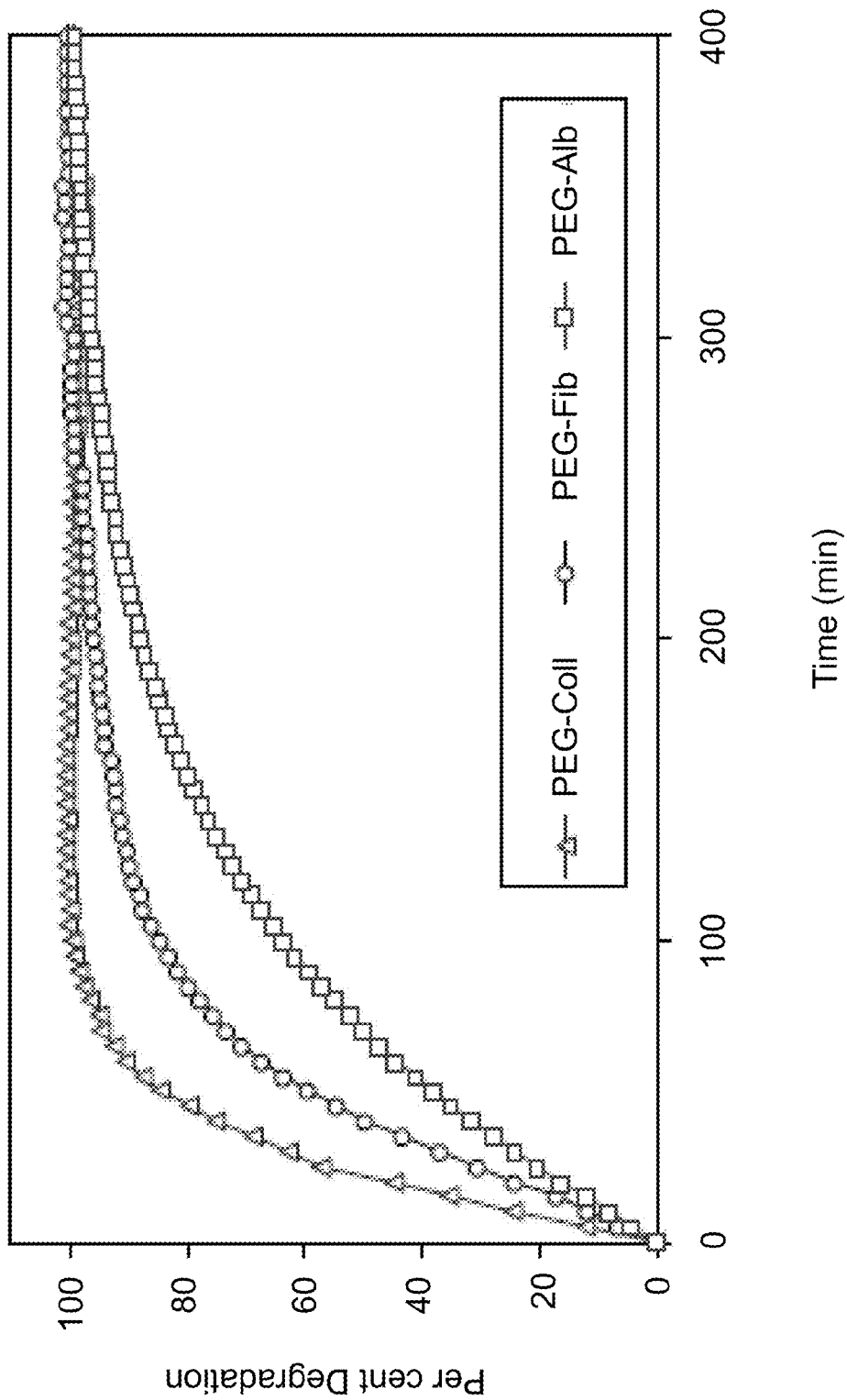
FIG. 3 presents a graph showing the degradation of PEGylated albumin (PEG-Alb), PEGylated fibrinogen (PEG-Fib) and PEGylated thiolated collagen (PEG-Coll) hydrogels as a function of time in a collagenase solution.

As shown in FIG. 2, for albumin, fibrinogen and thiolated collagen PEGylated precursors, the G' value increased immediately after the ultraviolet lamp was turned on, and reached a plateau after approximately two minutes, indicating the completion of the polymerization reaction.

Swelling Characterization:

Swelling experiments were performed on cylindrical plugs (5 mm in diameter) polymerized from 100 µl of PEGylated protein precursor. The hydrogel plugs were incubated in 10 ml PBS containing 0.1% sodium azide at room temperature for 24 hours. The wet weight of each plug was recorded before being lyophilized overnight. The dry weight was measured, and the swelling ration (Q) was calculated by dividing the dry weight by the wet weight after swelling. The estimated mass of PBS salts and sodium azide was subtracted from the dry weight. An additional swelling parameter, the % volume ratio, was defined as the % increase between the final volume of the plug as compared to the initial volume at the time of casting ($[V_{final}/V_{initial}] \times 100$).

The volume ratio of PEGylated thiolated collagen was 215±21%, whereas the swelling ratio was 145±27.

The volume ratio of PEGylated albumin was 238±27%, whereas the swelling ratio was 87±10.

In comparison, the volume ratio of PEGylated fibrinogen was 155±25%, whereas the swelling ratio was 179±29.

Biodegradation Characterization:

Biodegradation experiments were performed on cylindrical plugs with no cells made from fluorescently-labeled PEGylated protein as described by Peled et al. (2007). Briefly, 0.1 mg/ml succinimidyl acridine-9-carboxylate (SAC) (Pierce) was reconstituted in PBS containing DMSO to make a SAC staining solution. Each plug was incubated in the SAC staining solution overnight, followed by extensive washing in PBS and 0.1% sodium azide for 3 days. Each plug was incubated in 3 ml of 0.01 mg/ml collagenase type IA solution (Sigma-Aldrich) in PBS and 0.1% sodium azide at 37° C. with continuous agitation. A Varioscan spectral scanning multimode reader (Thermo Electron Corp.) was used to measure fluorescence intensity of the supernatant (excitation 364 nm, emission 460 nm) every 5 minutes for up to 10 hours. The raw data was normalized by the final fluorescence intensity of the fully degraded hydrogel. Two independent control groups were used to validate the experimental results: SAC-stained hydrogel plugs in PBS and sodium azide with no collagenase; and unstained hydrogel plugs in PBS, collagenase and sodium azide.

As shown in FIG. 3, the half-life of PEGylated thiolated collagen hydrogel in 0.01 mg/ml collagenase solution was 20 minutes, indicating significant biodegradability of the hydrogel. The half-life of PEGylated albumin hydrogel in the collagenase solution was 70 minutes, indicating a significantly lower biodegradability than the collagen hydrogel. In comparison, the half-life of PEGylated fibrinogen hydrogel under the same conditions was 40 minutes.

Cell Substrate Preparation (2-D):

Hydrogels made from PEGylated protein were used as substrates for 2-dimensional cultures of smooth muscle cells (SMCs). Sheep aortic SMCs were cultured up to 8$^{th}$ passage in Dulbecco's Modified Eagle Medium (DMEM) (Gibco, UK) containing 10% fetal bovine serum (FBS) (Biological Industries, Israel). Pre-cast hydrogels were made from PEGylated protein precursor solution (4 mg/ml), 10 kDa linear PEG-DA (10 mg/ml) and photoinitiator (0.1% w/v). The gels were attached to the bottom of a 24-well plate and seeded with a suspension of SMCs (70,000 cells per well) in 1 ml of culture medium. Cell spreading was monitored immediately after seeding using a phase-contrast microscope (Nikon Eclipse TS 100) and cell morphology was documented with a digital CCD camera.

Tissue culture plastic and PEG-only hydrogels were used as positive and negative controls, respectively, for cell spreading (data not shown).

Figure 4A:
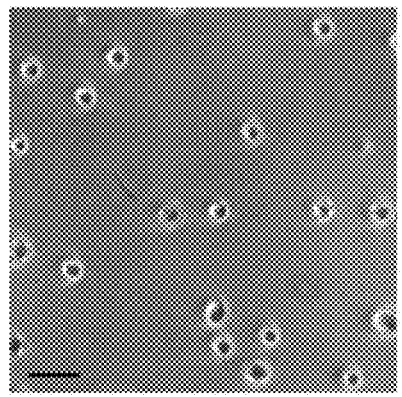
FIGS. 4A-F present phase contrast micrographs of smooth muscle cells on PEGylated albumin (FIGS. 4A and 4B), PEGylated thiolated collagen (FIGS. 4C and 4D) and PEGylated fibrinogen (FIGS. 4E and 4F) hydrogels, 2 hours (FIGS. 4A, 4C and 4E) and 24 hours (FIGS. 4B, 4D and 4F) after seeding cells on hydrogels; partial spreading 2 hours after seeding (FIGS. 4C and 4E), and full spreading 24 hours after seeding (FIGS. 4D and 4F) is observed on thiolated collagen and fibrinogen hydrogels whereas no spreading is observed on albumin hydrogel; scale bars equal 500 µm.
Figure 4B:
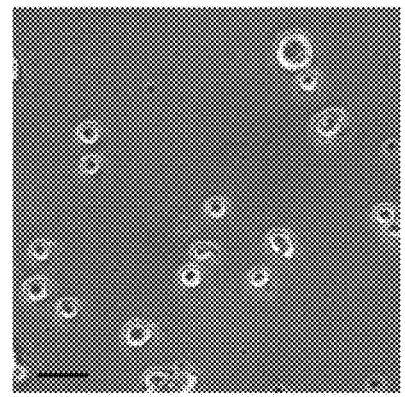
Figure 4C:
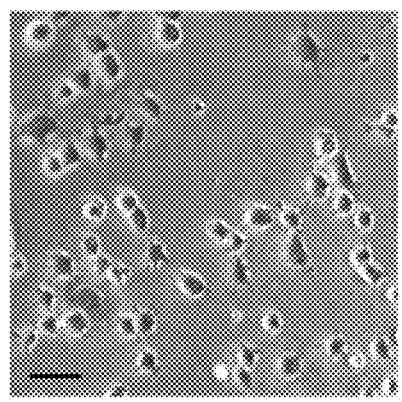
Figure 4D:
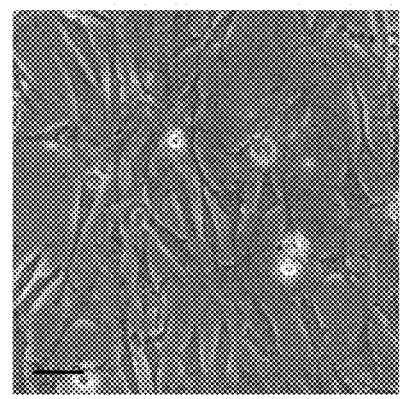
Figure 4E:
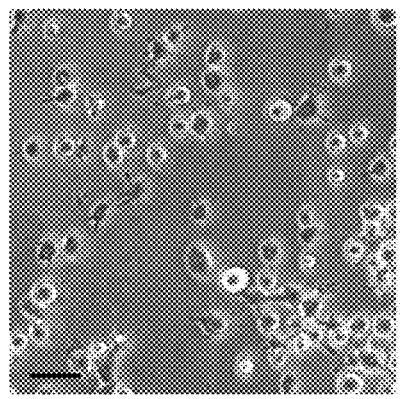
Figure 4F:
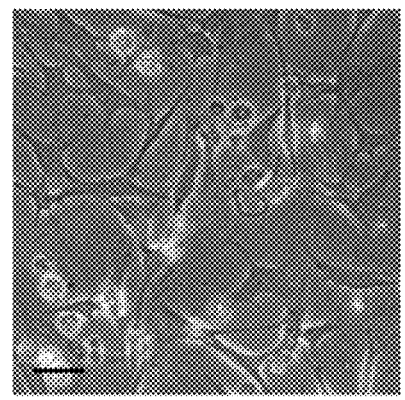

As shown in FIGS. 4C-F, cell spreading began immediately after seeding of SMCs on both PEGylated fibrinogen (FIG. 4E) and PEGylated collagen (FIG. 4C) hydrogels, and the cells were completely spread on the surface of both hydrogels after 24 hours (FIGS. 4D and 4F).

As shown in FIGS. 4A-B, no cell spreading occurred on PEGylated albumin hydrogel, even after 24 hours.

Cellularized Construct Preparation (3-D):

Cellularized constructs were made by photopolymerizing PEGylated protein precursor solution in the presence of dispersed SMCs. The passaged cells were trypsinized and suspended in 300 µl of PEGylated protein precursor (0.5× 10$^6$ cells per ml) containing photoinitiator (0.1% w/v). The cylindrical constructs were cast in 8 mm diameter sterile silicone tubes and transferred to a Petri dish containing culture medium. The encapsulated cells were monitored and documented daily using a phase-contrast microscope. Some experiments were continuously monitored using a custom-built time-lapse incubated microscope system (Nikon Eclipse TE-2000). Time-lapse experiments visually recorded active remodeling of cells in several locations within each hydrogel by sequentially imaging each field every 10 minutes for up to 96 hours.

Figure 5A:
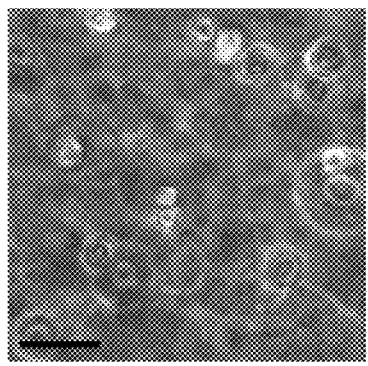
FIGS. 5A-I present phase contrast micrographs of smooth muscle cells encapsulated inside PEGylated albumin (FIGS. 5A-C), PEGylated thiolated collagen (FIGS. 5D-F) and PEGylated fibrinogen (FIGS. 5G-I) hydrogels, showing rounded cells immediately after seeding cells inside hydrogels (FIGS. 5A, 5D and 5G); cells with some extensions are observed 4 hours after seeding (FIGS. 5E and 5H), and fully extended and highly spindled cells are observed 24 hours after seeding (FIGS. 5G and 5I) in thiolated collagen and fibrinogen hydrogels whereas cells on albumin hydrogel remain rounded; scale bars equal 500 µm.
Figure 5B:
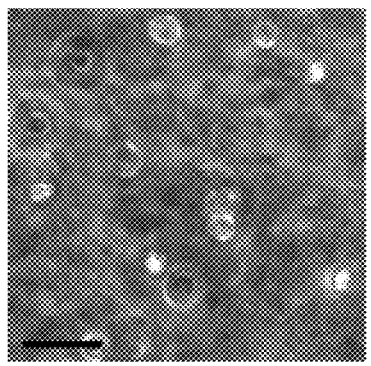
Figure 5C:
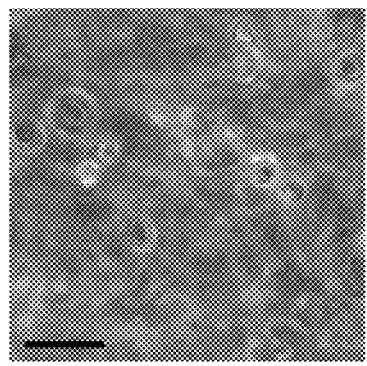
Figure 5D:
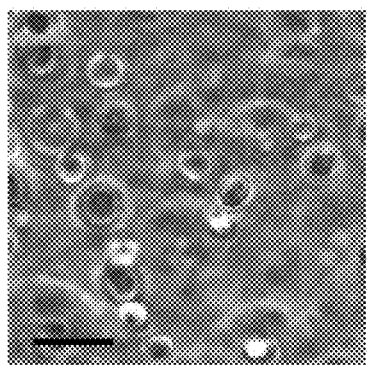
Figure 5E:
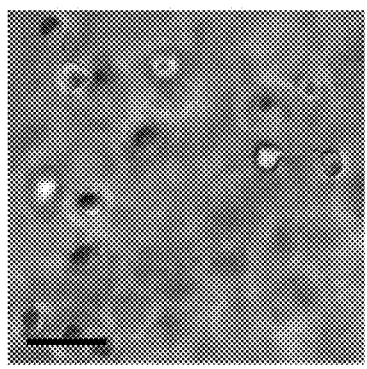
Figure 5F:
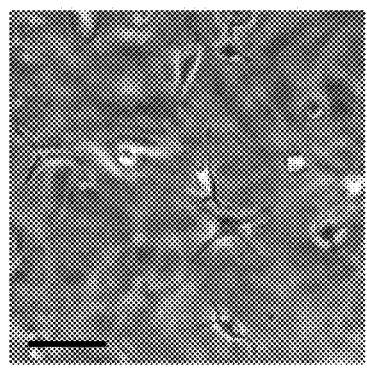
Figure 5G:
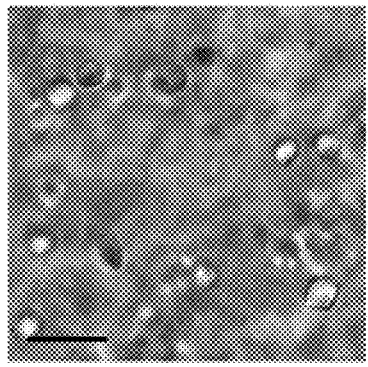
Figure 5H:
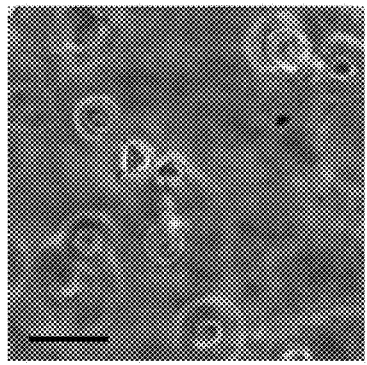
Figure 5I:
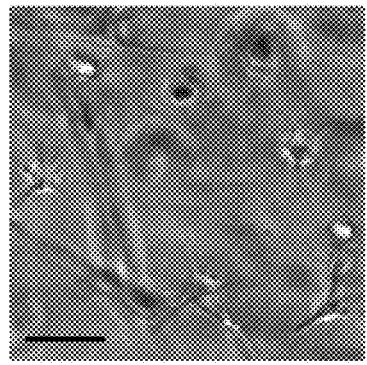

As shown in FIGS. 5E and 5H, extensions began to form after 4 hours on cells encapsulated in both PEGylated fibrinogen (FIG. 5H) and PEGylated collagen (FIG. 5E) hydrogel matrices. After 24 hours, the cells spread and became highly spindled in both hydrogel matrices (FIGS. 5F and 5I).

As shown in FIGS. 5B and 5C, no extensions formed in cells on an albumin hydrogel matrix, even after 24 hours.

Tissue Outgrowth Studies:

Outgrowth experiments were performed using dense tissue constructs made from compacted SMC-seeded collagen gels which were encapsulated inside PEGylated protein hydrogels. The collagen-based tissue was prepared from a solution of 5×DMEM (Biological Industries, Israel), 10% FBS, reconstituted type-I collagen solution in 0.1 N acetic acid, and 0.01 M NaOH with dispersed SMCs (0.5×10$^6$ cells per ml). The cell-seeded collagen gels were cultured for 2 days in 500 µl of medium before the compacted tissue was placed in 300 µl of PEGylated protein precursor solution and photoinitiator in a 48-well plate. After exposure to 5 minutes of ultraviolet light, the encapsulated tissue was cultured inside the hydrogel with 500 µl of culture medium. The cellular outgrowth experiments were monitored daily by phase contrast microscopy in order to visualize the penetration of the cells from the tissue into the surrounding hydrogel. The outgrowth results were quantified by measuring the average travel distance of the cells from the margins of the dense tissue into the PEGylated protein hydrogels, using phase contrast micrographs of the samples taken at set time intervals.

Figure 6A:
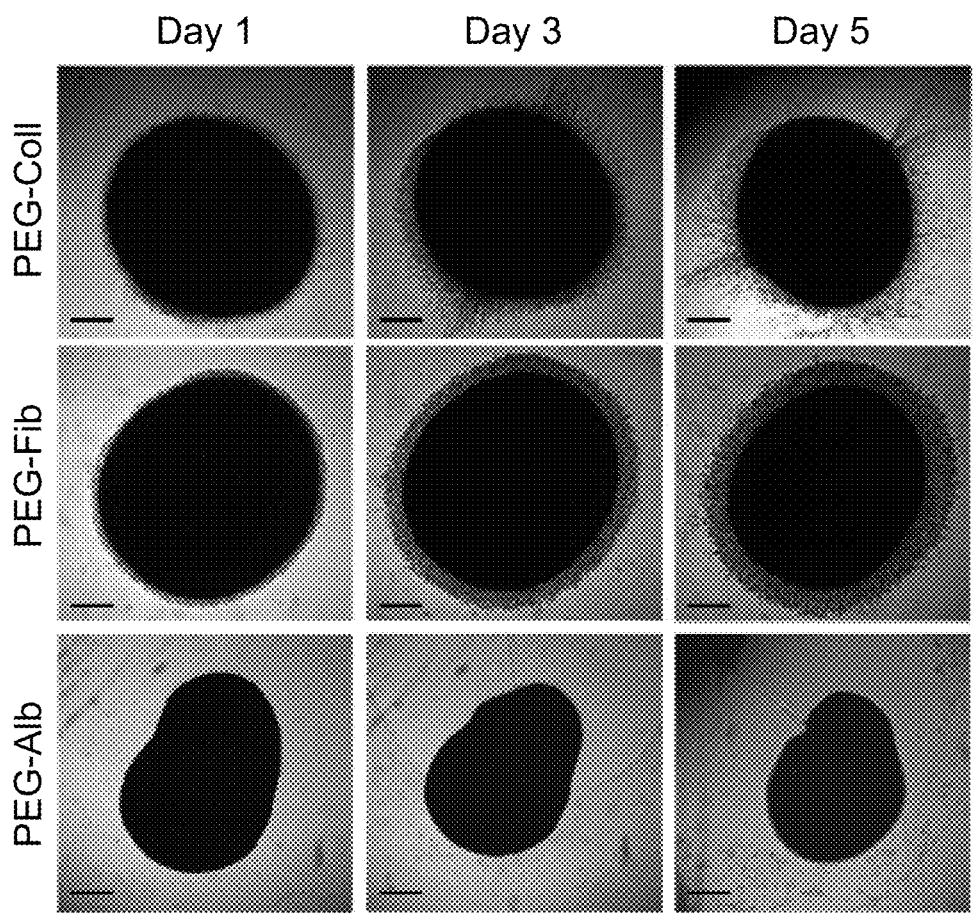
FIGS. 6A-C present phase contrast micrographs (FIGS. 6A and 6B) and a graph (FIG. 6C) showing smooth muscle cell invasion from dense tissue (dark) into PEGylated thiolated collagen (PEG-Coll), PEGylated fibrinogen (PEG-Fib) and PEGylated albumin (PEG-Alb) hydrogels (transparent)
Figure 6B:
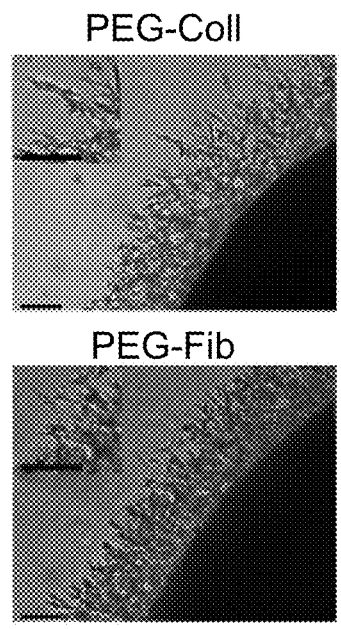
Figure 6C:
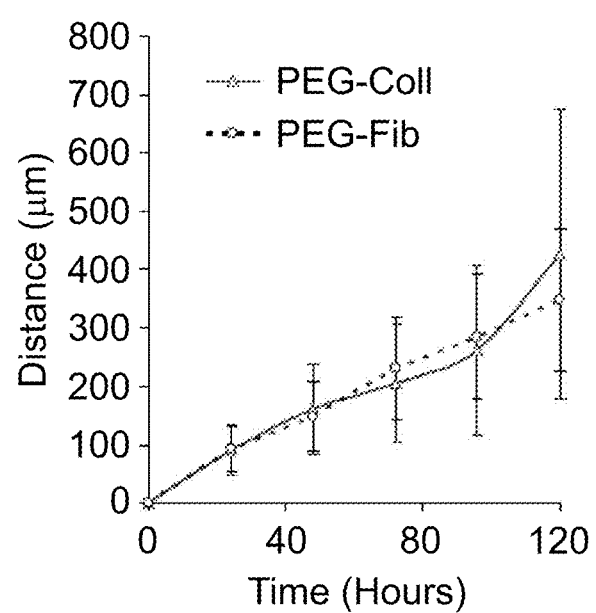

As shown in FIG. 6A, SMCs began to invade the PEGylated collagen matrix and the PEGylated fibrinogen matrix immediately after casting and continued to invade both matrices throughout the duration of the experiment. Quantitative measurements in the PEGylated fibrinogen and the PEGylated collagen matrices reveal highly similar patterns of migration (FIG. 6C). In contrast, no invasion of the PEGylated albumin matrix occurred, even after 5 days (FIG. 6A).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Buttafoco L, Engbers-Buijtenhuijs P, Poot A A, Dijkstra P J, Daamen W F, van Kuppevelt T H, et al. First steps towards tissue engineering of small-diameter blood vessels: preparation of flat scaffolds of collagen and elastin by means of freeze drying. *J Biomed Mater Res B Appl Biomater* 2006; 77(2):357-368.

Drury J L, Mooney D J. Hydrogels for tissue engineering: scaffold design variables and applications. *Biomaterials* 2003; 24(24):4337-4351.

D'Urso E M, Jean-Francois J, Doillon C J, Fortier G. Poly(ethylene glycol)-serum albumin hydrogel as matrix for enzyme immobilization: biomedical applications. *Artif Cells Blood Substit Immobil Biotechnol.* 1995; 23(5):587-595.

Elbert D L, Hubbell J A. Conjugate addition reactions combined with free-radical cross-linking for the design of materials for tissue engineering. *Biomacromolecules* 2001; 2(2):430-441.

Elisseeff J, McIntosh W, Anseth K, Riley S, Ragan P, Langer R. Photoencapsulation of chondrocytes in poly(ethylene oxide)-based semi-interpenetrating networks. *J Biomed Mater Res* 2000; 51(2):164-171.

Friess W. Collagen—biomaterial for drug delivery. *Eur J Pharm Biopharm* 1998; 45(2):113-136.

Gayet J C, Fortier G. Drug release from new bioartificial hydrogel. *Artif Cells Blood Substit Immobil Biotechnol.* 1995; 23(5):605-11.

Hubbell J A. Materials as morphogenetic guides in tissue engineering. *Curr Opin Biotechnol* 2003; 14(5):551-558.

Jean-Francois J, Fortier G. Immobilization of L-asparaginase into a biocompatible poly(ethylene glycol)-albumin hydrogel: I: Preparation and in vitro characterization. *Biotechnol Appl Biochem.* 1996; 23 (Pt 3):221-6.

Jean-Francois J, D'Urso E M, Fortier G. Immobilization of L-asparaginase into a biocompatible poly(ethylene glycol)-albumin hydrogel: evaluation of performance in vivo. *Biotechnol Appl Biochem.* 1997; 26 (Pt 3):203-12.

Lutolf M P, Hubbell J A. Synthesis and Physicochemical Characterization of End-Linked Poly(ethylene glycol)-co-peptide Hydrogels Formed by Michael-Type Addition. *Biomacromolecules* 2003; 4(3):713-722.

Ma L, Gao C, Mao Z, Zhou J, Shen J. Enhanced biological stability of collagen porous scaffolds by using amino acids as novel cross-linking bridges. *Biomaterials* 2004; 25(15):2997-3004

Merrill E A, Salzman E W. Polyethylene oxide as a biomaterial. *ASAIO J* 1983; 6:60-64.

Nguyen K T, West J L. Photopolymerizable hydrogels for tissue engineering applications. *Biomaterials* 2002; 23(22):4307-4314.

Nicolas F L, Gagnieu C H. Denatured thiolated collagen. II. Cross-linking by oxidation. *Biomaterials* 1997; 18(11): 815-821.

Nimni M E, Cheung D, Strates B, Kodama M, Sheikh K. Chemically modified collagen: a natural biomaterial for tissue replacement. *J Biomed Mater Res* 1987; 21(6):741-771.

Park S N, Park J C, Kim H O, Song M J, Suh H. Characterization of porous collagen/hyaluronic acid scaffold modified by 1-ethyl-3-(3-dimethylaminopropyl)carbodiimide cross-linking *Biomaterials* 2002; 23 (4): 1205-1212.

Pieters M, Jerling J C, Weisel J W. Effect of freeze-drying, freezing and frozen storage of blood plasma on fibrin network characteristics. *Thromb Res* 2002; 107(5):263-269.

Sachlos E, Czernuszka J T. Making tissue engineering scaffolds work. Review: the application of solid freeform fabrication technology to the production of tissue engineering scaffolds. *Eur Cell Mater.* 2003; 5:29-39.

Schoof H, Apel J, Heschel I, Rau G. Control of pore structure and size in freeze-dried collagen sponges. *J Biomed Mater Res* 2001; 58(4):352-357.

Temenoff J S, Athanasiou K A, LeBaron R G, Mikos A G. Effect of poly(ethylene glycol) molecular weight on tensile and swelling properties of oligo(poly(ethylene glycol) fumarate) hydrogels for cartilage tissue engineering. *J Biomed Mater Res* 2002; 59(3):429-437.

What is claimed is:

1. A composition comprising a scaffold, said scaffold comprising a plurality of albumin molecules and a plurality of synthetic polymers covalently attached to said albumin molecules, each of said albumin molecules being covalently attached to at least two of said synthetic polymers, wherein said synthetic polymers are cross-linked with each other, wherein said albumin is denatured, and wherein a concentration of said scaffold in the composition is in a range of 3 mg/ml to 50 mg/ml.

2. The composition of claim 1, wherein a concentration of said scaffold in the composition is 3 mg/ml to 30 mg/ml.

3. The composition of claim 1, wherein said concentration of said scaffold in the composition is 3 mg/ml.

4. The composition of claim 1, wherein said concentration of said scaffold in the composition is 30 mg/ml to 50 mg/ml.

5. The composition of claim 1, wherein said synthetic polymer is PEG.

6. The composition of claim 1, wherein said at least two synthetic polymers are covalently attached to a cysteine of said albumin.

7. A composition comprising a scaffold comprising a plurality of albumin molecules and a plurality of synthetic polymers covalently attached to said albumin molecules, each of said albumin molecules being covalently attached to at least two of said synthetic polymers, wherein said synthetic polymers are cross-linked with each other, and wherein said albumin is denatured.

8. The composition of claim 7, wherein said albumin is denatured by exposure to a denaturing agent selected from the group consisting of urea and guanidine chloride.

\* \* \* \* \*